United States Patent [19]

Douglas et al.

[11] Patent Number: 4,927,970

[45] Date of Patent: May 22, 1990

[54] SUBSTITUTED 3-CYCLOBUTENE-1,2-DIONE INTERMEDIATES

[75] Inventors: James L. Douglas, Montreal West, Canada; Guy Fabre, Saint Jean de Vadas; Claude Demosthene, Aramon, both of France

[73] Assignee: Bristol-Myers Company, New York, N.Y.

[21] Appl. No.: 174,443

[22] Filed: Apr. 11, 1988

Related U.S. Application Data

[63] Continuation-in-part of Ser. No. 50,670, May 14, 1987, abandoned.

[51] Int. Cl.$^5$ .................. C07C 87/36; C07C 87/452
[52] U.S. Cl. ........................ 564/462; 564/1; 564/341; 564/428
[58] Field of Search ............... 564/336, 337, 338, 341, 564/428, 462, 1; 546/236

[56] References Cited

U.S. PATENT DOCUMENTS

| | | | |
|---|---|---|---|
| 4,092,146 | 5/1978 | Fischer et al. | 568/315 |
| 4,390,701 | 6/1983 | Algieri et al. | 546/235 |
| 4,395,553 | 7/1983 | Algieri et al. | 546/235 |
| 4,521,625 | 6/1985 | Brown et al. | 564/461 |
| 4,522,943 | 6/1985 | Algieri et al. | 514/183 |
| 4,526,973 | 7/1985 | Algieri et al. | 546/235 |
| 4,656,180 | 4/1987 | Postius et al. | 564/306 |
| 4,788,184 | 11/1988 | Algieri et al. | 548/526 |

*Primary Examiner*—John Kight, III
*Assistant Examiner*—Nathan M. Nutter
*Attorney, Agent, or Firm*—Aldo A. Algieri

[57] ABSTRACT

The present invention relates to novel intermediates of the formula

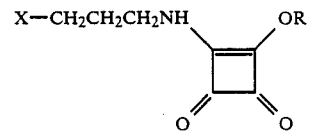

wherein R is lower alkyl or cyclohexyl, and X is hydroxy or a conventional leaving group, and the use thereof in a process for the preparation of certain histamine $H_2$-antagonists.

10 Claims, No Drawings

SUBSTITUTED 3-CYCLOBUTENE-1,2-DIONE INTERMEDIATES

CROSS-REFERENCE TO RELATED APPLICATION

This application is a continuation-in-part of our prior, co-pending application Ser. No. 050,670 filed May 14, 1987 and now abandoned.

BACKGROUND OF THE INVENTION

1. Field of the Invention

The present invention provides novel intermediates and their use in the preparation of certain histamine $H_2$-antagonists which are useful in the treatment of peptic ulcers and other conditions caused or exacerbated by gastric acidity.

2. Disclosure Statement

Our colleagues A. A. Algieri and R. R. Crenshaw disclose histamine $H_2$-receptor antagonists in U.S. Pat. No. 4,390,701 issued June 28, 1983, U.S. Pat. No. 395,553 issued July 26, 1983, U.S. Pat. No. 4,522,943 issued June 11, 1985 and U.S. Pat. No. 4,526,973 issued July 2, 1985 which are substantially the same as those described by the present invention.

U.S. Pat. No. 4,521,625 issued June 4, 1985 to T. H. Brown and R. C. Young discloses intermediates of the formula

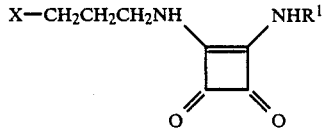

wherein $R^1$ is hydrogen or a $C_{1-6}$ alkyl group and X is hydroxy or a group displaceable by hydroxy or the equivalent thereof which are used in a process for the preparation of compounds which are substantially the same as those described in the above-mentioned U.S. patents.

The novel intermediates provided in the present invention are useful in an improved process for the preparation of histamine $H_2$-antagonists described herein.

SUMMARY OF THE INVENTION

Histamine $H_2$-receptor antagonists of the formula

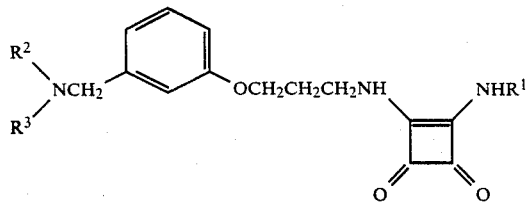

wherein $R^1$ is hydrogen or lower alkyl and $R^2$ and $R^3$ are as defined below, which are useful in treating peptic ulcers, are prepared via a new process from novel intermediates of the formula

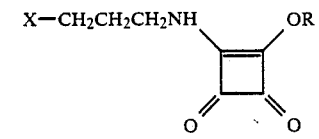

in which R is lower alkyl or cyclohexyl and X is a hydroxy or a conventional leaving group.

DESCRIPTION OF THE INVENTION

The present invention relates to novel intermediates which are useful in the preparation of certain histamine $H_2$-antagonists which are described herein. Accordingly, the present invention provides compounds of the formula

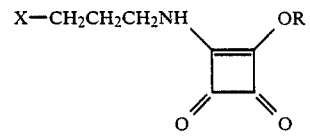

wherein R is lower alkyl or cyclohexyl, and X is hydroxy or a conventional leaving group.

Preferably R is $C_{1-6}$ alkyl and, most preferably, R is butyl, sec-butyl or neopentyl. Suitable conventional leaving groups are well-known to those skilled in the art. Preferably, X is hydroxy, bromo, iodo, chloro, or $-O_3SR^4$ in which $R^4$ is lower alkyl, trifluoromethyl, phenyl or substituted phenyl and, most preferably, X is bromo or benzenesulfonate.

In the present invention, as used herein and in the claims, the term "lower alkyl" means straight or branched chain alkyl containing from 1 to 8 carbon atoms. Preferably they contain from 1 to 6 atoms and, most preferably, they contain 1 to 5 carbon atoms. The term "halogen" as used herein and in the claims is intended to include bromine, chlorine and iodine. Unless otherwise specified in the particular instance, the terms "butyl" and "butoxy" as used herein and in the claims is intended to mean n-butyl and n-butoxy. The use of the terms "butyl" and "butoxy" are only a convenience and are not intended to exclude other $C_4$ alkyl groups from the scope of the present invention.

The compounds of the formula I may be prepared from the compounds of formula II as illustrated in Scheme 1.

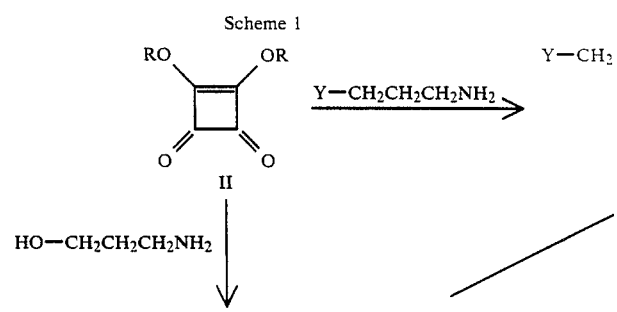

-continued
Scheme 1

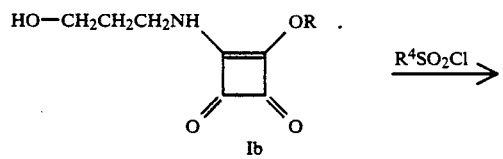

Scheme 2

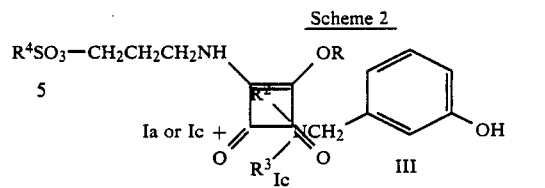

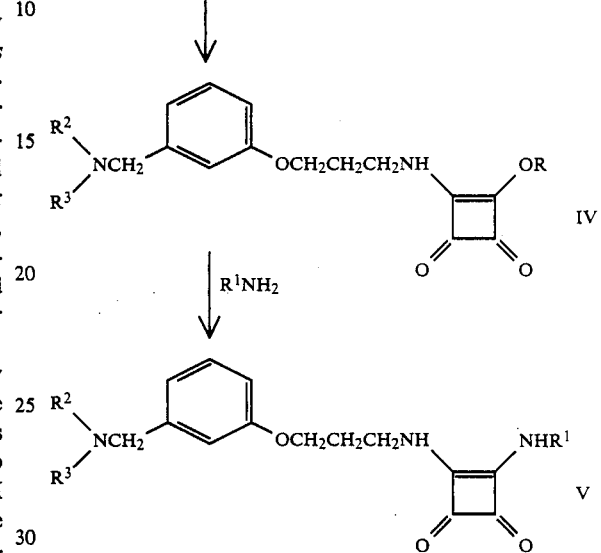

The compounds of Formula II may be prepared by the procedures described by G. Maahs, *Justus Liebigs Ann. Chem.*, 686, 55 (1965) and A. H. Schmidt, *Synthesis*, 869 (1978). In reaction Scheme 1, R is cyclohexyl or lower alkyl, for example, methyl, ethyl, propyl, isopropyl, butyl, sec-butyl, tertiary-butyl, neopentyl, pentyl and the like; Y is halogen and preferably bromo or chloro and $R^4$ is lower alkyl [e.g. methyl or ethyl], trifluoromethyl, phenyl or substituted phenyl [e.g. p-bromobenzene or p-toluenesulfonate] in which said substituent may be methyl, chloro, bromo, methoxy or nitro.

The compounds of formula I which are conveniently illustrated in Scheme 1 by formulas Ia, Ib and Ic may be prepared from compounds of formula II by various reaction routes. Thus, compounds of the formula Ib may readily be prepared from a compound of formula II by reacting with 3-amino propanol in a non-reactive solvent such as methanol, ethanol, 1-butanol, acetonitrile, toluene or tetrahydrofuran at a temperature from 0° C. to about the reflux temperature of the solvent and preferably at ambient temperature.

Compounds of the formula Ia may be prepared from compounds of the formula II by reacting with about one equivalent of 3-chloropropylamine hydrochloride or 3-bromopropylamine hydrobromide which are preferably neutralized just before use in situ with a tertiary amine or inorganic base in an inert organic solvent such as dichloromethane, methanol, ethanol, tetrahydrofuran and dimethylformamide. Alternatively, the compounds of formula Ia may be prepared from the compounds of formula Ib by reacting with a suitable halogenating agent, for example, thionyl chloride or thionyl bromide in an inert organic solvent such as dichloromethane, chloroform or tetrahydrofuran and preferably in the presence of a base such as tertiary amine (e.g., triethylamine, pyridine and lutidine) or inorganic base (e.g., sodium carbonate and potassium carbonate) at a temperature of 0° C. to about the reflux temperature of the solvent.

The compounds of formula Ic are conveniently prepared from compounds of formula Ib by reacting with sulfonating agents such as methanesulfonyl chloride, benzenesulfonyl chloride, p-toluenesulfonyl chloride, p-bromobenzenesulfonyl chloride and p-nitrobenzenesulfonyl chloride. The reaction is conducted in a non-reactive solvent such as dichloromethane, acetonitrile, tetrahydrofuran and dimethylformamide and preferably in the presence of a tertiary amine or inorganic base to remove the acid which is produced.

In another aspect, the present invention provides a process for the preparation of histamine $H_2$-antagonist compounds of the formula V as shown in Scheme 2.

In reaction Scheme 2, a compound of formula III is reacted with a compound of formula Ia or Ic to produce the intermediate of formula IV which is then treated with an amine of the formula $R^1NH_2$ produce the desired histamine $H_2$-antagonist of the formula V wherein $R^1$ is hydrogen or lower alkyl, and, $R^2$ and $R^3$ are lower alkyl, or $R^2$ and $R^3$, taken together with the nitrogen to which they are attached, may be pyrrolidino, methylpyrrolidino, piperidino, methylpiperidino, homopiperidino, heptamethyleneimino or octamethyleneimino, or a non-toxic pharmaceutically acceptable salt thereof.

The compounds of formula III may be prepared by the methods of Turner et al., *J. Org. Chem.*, 24. 1952 (1959) and United Kingdom patent application GB No. 2,023,133 or, preferably, by the method described herein for the compound of formula III wherein $R^2$ and $R^3$ are joined together with the nitrogen atom to form a piperidino group.

The reaction of a compound of formula III with a compound of formula Ia or Ic may preferably be conducted in the presence of a base and optionally in the presence of a catalyst in a non-reactive solvent such as methanol, ethanol, acetone, methyl ethyl ketone, toluene, chloroform, dichloromethane, ethylene chloride, tetrahydrofuran, dimethylformamide and mixed aqueous-organic solvents. The preferred solvent systems are 1,2-dichloroethane-water and dichloromethane-water. The reaction is preferably conducted in the presence of a base such as sodium hydroxide, potassium hydroxide, pyridine, sodium carbonate, sodium bicarbonate, potassium carbonate, potassium bicarbonate, potassium fluoride on alumina and potassium fluoride on silica. Most preferably, the reaction is conducted in the presence of about one to two equivalents of a mild base such as potassium carbonate. Furthermore, we have found that the use of powdered (pulverized) potassium carbonate rather than the granular form is most preferred in non-aqueous solvents such as tetrahydrofuran and dichloromethane.

The reaction of a compound of formula III with a compound of formula Ia is preferably conducted in the presence of an effective amount of a catalyst such as sodium iodide, tetrabutylammonium bromide, tetrabutylammonium chloride, Aliquat 336 (which is a registered trademark of Henkel Corporation for tricaprylylmethylammonium chloride), benzyltributylammonium bromide, benzytriethylammonium chloride and 18-Crown-6 (1,4,7,10,13,16-hexaoxacyclooctadecane). Especially preferred catalyst are tris[2-(2-methoxyethoxy)ethyl]amine and benzyltributylammonium bromide. Suitably, an amount of catalyst up to one equivalent may be used and, most preferably, an amount of about 0.05 to 0.2 equivalent.

The temperature of the reaction is not critical and may be conducted from about 0° C. to the reflux temperature of the solvent for a period of hours to 7 days depending on the reaction conditions utilized.

An especially preferred reaction condition which we have discovered is the use of the catalysts, tris[2methoxyethoxy)ethyl]amine in combination with a mild base such as powdered potassium carbonate in dichloromethane at ambient temperature.

The desired compound of formula V is then prepared by standard procedures by reacting a compound of formula IV with the appropriate amine in a non-reactive solvent such as methanol, ethanol and dimethylformamide.

DESCRIPTION OF SPECIFIC EMBODIMENTS

Preparation 1: 1-Piperidinomethyl-3-phenol

Piperidine (50 mL, 0.50 mole) was added dropwise to a stirred solution of 3-hydroxybenzaldehyde (30.0 g, 0.246 mole) in dimethylformamide (40 mL) with cooling to maintain the temperature below 45° C. The solution was heated at 50° C. for 15 minutes then cooled to 40° C. A solution of formic acid (97%, 25 mL. 0.64 mole) and water (2 mL) was added dropwise with stirring while the temperature was maintained at 40° C. with cooling. The resulting stirred solution was heated slowly (vigorous gas evolution commenced at about 60° C.) to 110°–115° C. and maintained at that temperature for 1.5 hours. The solution was cooled to 40° C. and was added to 300 mL of water at 0° C. with vigorous stirring. Aqueous 25% sodium hydroxide was added until the reaction mixture was at pH 9.4 and stirring was continued for 1.5 hours at ambient temperature. The mixture was cooled to 0° C. over 1 hour and the solid was collected by filtration, washed thoroughly with water (0° C., 300 mL)), and dried in vacuo to give 43.7 g of the desired product.

The product was dissolved in 2-propanol (115 mL) by heating to reflux, filtered (washed through with 15 mL hot 2-propanol), and cooled slowly to 0° C. with stirring. The solid was collected by filtration, washed with 2-propanol (0° C., 40 mL)) and dried in vacuo to give 32.96 g (70.0% yield) of the title compound; m.p.=135°–137° C.

Preparation 2: 1-Piperidinomethyl-3-phenol

A mixture of toluene (300 mL), piperidine (125 mL, 107 g, 1.25 moles) and 3-hydroxybenzaldehyde (122 g, 1.0 mole) was heated with stirring at 50°–55° C. for 30 minutes. The reaction mixture was cooled to about 15° C. and 90% formic acid (108 mL; 127 g, 2.54 moles) was added slowly while maintaining the temperature below 20° C. The mixture was heated to reflux and the water formed (about 34 mL) was collected by azeotropic distillation. After cooling to about 40° C., water (2L) was added, then the solution was cooled to 10° C. and basified to pH 9-10 with aqueous 50% sodium hydroxide. After stirring at ambient temperature for 18 hours, the mixture was cooled to 3° C. and the solids were collected by filtration, washed with water and dried in vacuo at 50° C. to give 190 g of product. Recrystallization from methanol-acetonitrile (2:1) using decolorizing carbon yielded 168 g (88% yield) of the title compound: m.p.=136°–139° C.

Anal Calcd. for $C_{12}H_{17}NO$: C, 75.33; H, 8.g6; N, 7.32. Found: C, 75.25; H, S.82; N, 7.32.

EXAMPLE 1

1-Butoxy-2-(3-bromopropylamino)-1-cyclobutene-3,4-dione

A. 1,2-Dibutoxy-1-cyclobutene -3,4-dione

A mixture of 1-butanol (48 mL), toluene (32 mL), and 1,2-dihydroxy-l-cyclobutene-3,4-dione (16.0 g, 0.1402 mole) was heated at reflux under a nitrogen atmosphere with stirring under a Dean-Stark water separator until water stopped passing over. The resulting solution of the title compound was cooled to 0°–5° C.

B. 1-Butoxy-2-(3-bromopropylamino)-1-cyclobutene-3,4-dione

Solid 3-bromopropylamine hydrobromide (31.0 g, 0.1416 mole) was added with stirring to a solution of sodium hydroxide (5.77 g, 0.140 mole) in methanol (152 mL) and stirred at ambient temperature for 15 minutes. The solution was cooled to 0°–5° C. and then added with stirring to the solution of Step A. The mixture was stirred at 22° C. for 1.5 hours then concentrated under reduced pressure (40° C.) to about 120 mL volume. Toluene (120 mL) was added and the mixture was washed with water (240 mL). The organic layer was dried (sodium sulfate), filtered, and the solvent was evaporated under reduced pressure to give 38.64 g (95.0 % yield) of the title compound as an off-white solid. The product was used without further purification in the subsequent reaction.

A sample was recrystallized from methanol at −60° C. to give pure title compound; m.p.=56°–57° C. (crystal form changes), 68° C. (melting complete).

Anal. Calcd. for $C_{11}H_{16}BrNO_3$: C, 45.53; H, 5.56; N, 4.83; Br, 27.54. Found: C, 45.59; H, 5.55; N, 4.81; Br, 27.41.

EXAMPLE 2

1-Butoxy-2-[3-(3-piperidinomethylphenoxy)-propylamino]-1-cyclobutene-3,4-dione

A slurry of 1-butoxy-2-(3-bromopropylamino)-1-cyclobutene-3,4-dione [prepared in Example 1] (5.0 g, 0.01723 mole), 1-piperidinomethyl-3-phenol (3.395 g, 0.01723 mole) tetrabutylammonium bromide (0.55 g, 0.0017 mole) dichloromethane (50 mL), and 0.33M sodium hydroxide (52.5 mL, 0.0175 mole) was stirred vigorously and heated at reflux temperature for 4 days. The mixture was cooled to ambient temperature, the phases were separated, and the aqueous phase was extracted with dichloromethane (15 mL). The combined organic layers were washed with 0.5M sodium hydroxide (2×50 mL) and water (50 mL). Each aqueous wash was extracted with 10 mL of dichloromethane. The combined organic extracts were dried (sodium sulfate), filtered, and taken to a total volume of 95 mL with more dichloromethane. Methanol (5 mL) followed by silica gel 60 (70–230 mesh, activity 2–3, 5.2 g) was added and stirred briefly. The mixture was filtered and the filter cake was washed with 5% methanol in dichloromethane (50 mL). The filtrate was evaporated under reduced pressure to give 4.06 g (58.8% yield) of the title compound as a brown gum. A sample of the product purified by chromatography was obtained as a yellow gum.
$^1H$ NMR(CDCl$_3$,δ):0.97(3H,t), 1.2–2.1(16H,m), 2.4(4H,m), 3.51(2H,s), 3.7(2H,m), 4.07(2H,t), 4.67(2H,t), 6.3–7.0(4H,m), 7.1 (1H,broad).

EXAMPLE 3

1-Amino-2-[3-(3-piperidinomethylphenoxy)-propylamino]-1-cyclobutene-3,4-dione hydrochloride

A.

1-Amino-2-[3-(3-piperidinomethylphenoxy)-propylamino]-1-cyclobutene-3,4-dione

To a solution of 1-butoxy-2-[3-(3-piperidinomethylphenoxy)propylamino]-1-cyclobutene-3,4-dione [prepared in Example 2] (4.06 g, 0.01014 mole) in methanol (40 mL) was added 14M aqueous ammonium hydroxide (1.5 mL, 0.021 mole). The mixture was stirred at ambient temperature for 41 hours. Water (40 mL) was added and stirring was continued for 10 minutes. The precipitate was collected by filtration, washed with methanol:water (1:1) (20 mL), and dried in vacuo to give 2.68 g (77.0% yield) of the title compound. A sample purified by chromatography showed spectral data identical to that of an authentic sample.

B.

1-Amino-2-[3-(3-piperidinomethylphenoxy)-propylamino)-1-cyclobutene-3,4-dione hydrochloride A mixture of 1-amino-2-[3-(3-piperidinomethylphenoxy)-propylamino]-1-cyclobutene-3,4-dione [prepared in Step A] (2.68 g, 0.0078 mole), 2-propanol (8.5 mL), and 1M aqueous hydrochloric acid (8.0 mL, 0.008 mole) was heated to reflux with stirring. Insoluble material was removed by filtration and acetone (24 mL) was added to the hot solution. The mixture was stirred at ambient temperature for 18 hours, then cooled to 0° C. The solid was collected by filtration, washed with acetone:2-propanol (2:1) (3 mL), and dried in vacuo to give 1.67 g (56.4% yield) of the title compound as an off-white powder. The product was shown by spectral data to be identical to authentic sample of the hydrochloride salt.

EXAMPLE 4

1-Butoxy-2-[3-(3-piperidinomethylphenoxy)-propylamino]-1-cyclobutene-3,4-dione

A mixture of 1-butoxy-2-(3-bromopropylamino)-1-cyclobutene-3,4-dione (1.0 g, 0.00345 mole), 1-piperidinomethyl-3-phenol (0.66 g, 0.00345 mole), dimethylformamide (5 mL), potassium carbonate (0.63 g, 0.0046 mole) and sodium iodide (100 mg, 0.00067 mole) was stirred at ambient temperature for 24 hours. Analysis of the reaction mixture by thin layer chromatography showed little or no reaction to have occurred. The reaction mixture was heated at 70° C. for 5 hours then diluted with water and extracted with ethyl acetate. The organic extracts were washed several times with water and brine, dried, and the solvent was evaporated under reduced pressure to give the title compound. The desired product which is identical to Example 2 could be isolated by chromatography in about 20% yield.

EXAMPLE 5

1-Butoxy-2-(3-bromopropylamino)-1-cyclobutene-3,4-dione

A. 1,2-Dibutoxy-1-cyclobutene-3,4-dione

Protected by a nitrogen atmosphere, a mixture of 1-butanol (64 mL), toluene (42 mL), and 1,2-dihydroxy-1-cyclobutene-3,4-dione (21.43 g, 0.1878 mole) was heated under reflux with stirring under a Dean-Stark water separator until water stopped passing over (7.6 mL of water was collected). Reflux was continued for a further 30 minutes, then the excess toluene and butanol were distilled off under reduced pressure (50–100 mm Hg) to give the title compound as a yellow liquid. The concentrate was diluted with 25 mL of methanol.

B.

1-Butoxy-2-(3-bromopropylamino)-1-cyclobutene-3,4-dione

Solid 3-bromopropylamine hydrobromide (41.52 g, 0.1897 mole) was added with stirring to a solution of sodium hydroxide (7.73 g, contains 0.187 mole) in methanol (150 mL) at 22° C., stirred for 15 minutes, then cooled to 0° C. to give a hazy solution of bromopropylamine base. The solution of bromopropylamine base was added slowly (over 20 minutes) with vigorous stirring to the product of Step A in methanol at 0° C. The mixture was stirred at 22° C. for 1.5 hours, polish filtered through diatomaceous earth (washed through with 50 mL of methanol) and added with vigorous stirring to water (1060 mL). The stirred mixture was cooled to −10° C. over several hours. The solid was collected by filtration, washed well with water (0° C., 440 mL) and dried in vacuo to give 50.0 g (91.8% yield) of the title compound as an off-white solid; m.p.=66°–68° C.

EXAMPLE 6

1-Amino-2-[3-(3-piperidinomethylphenoxy)-propylamino]-1-cyclobutene-3,4-dione

A.

1-Butoxy-2-[3-(3-piperidinomethylphenoxy)-propylamino]-1-cyclobutene-3,4-dione

A solution of 1-butoxy-2-(3-bromopropylamino)-1-cyclobutene-3,4-dione [prepared in Example 5] (50.0 g, 0.1723 mole) in dichloromethane was polish filtered (total volume of dichloromethane used: 250 mL). A solution of sodium bicarbonate (28.5 g, 0.339 mole) in 300 mL of water, solid 1-piperidinomethyl-3-phenol (32.96 g, 0.1723 mole), and solid tetrabutylammonium bromide (5.5 g, 0.017 mole) were added. The mixture was stirred vigorously and heated under reflux for 72 hours. The organic layer was separated from the cooled (22° C.) mixture. The aqueous layer was re-extracted with 50 mL of dichloromethane. The combined organic layers were washed twice with 250 mL each of 0.5M sodium hydroxide, then dried (sodium sulfate), filtered and made up to a total volume of 350 ML with dichloromethane (ca. 10 mL required). Methanol (35 mL) followed by silica gel 60 (70 g, 70–230 mesh, activity 3–4) was added. After thorough mixing, the silica gel was removed by filtration and re-extracted with a further 400 mL of 10% methanol in dichloromethane. The combined organics were concentrated to small volume in vacuo, methanol was added (ca. 50 mL), and the solution was re-concentrated to small volume to give the title compound as a crude concentrate in methanol.

B.

1-Amino-2-[3-(3-piperidinomethylphenoxy)-propylamino]-1-cyclobutene-3,4-dione

The crude concentrate of 1-butoxy-2-[3-(3-piperidinomethylphenoxy)propylamino]-1-cyclobutene-3,4-dione [prepared in Step A] was diluted to a total volume of 370 mL with methanol (ca. 340 mL required). Concentrated aqueous ammonia (13.9M, 15.0 mL, 0.208 mole) was added dropwise with vigorous stirring at 22° C. Stirring was continued for 26 hours at 22° C. The resulting orange slurry was diluted with water (500 mL), cooled to 22° C., and stirring was continued for a further 30 minutes. The solid was collected by filtration, washed with water: methanol (60:40) (150 mL) and dried in vacuo to give 36.44 g (61.6% yield) of title compound.

EXAMPLE 7

1-Butoxy-2-(3-hydroxypropvlamino)-1-cyclobutene-3,4-dione

A slurry of 1,2-dihydroxy-1-cyclobutene-3,4-dione (15.0 g, 131.5 mmol), 45 mL of 1-butanol and 30 mL of toluene was heated at reflux under a nitrogen atmosphere with stirring under a Dean-Stark Water separator until water stopped passing over. The reaction mixture was then cooled to 0° C. and a solution of 3-amino-1-propanol (9.88 g, 131.5 mmol) in 10 mL of 1-butanol was added dropwise. After 1 hour at ambient temperature, charcoal was added and the mixture filtered through a pad of diatomaceous earth. The filtrate was evaporated under reduced pressure to give 28.9 g of the title compound as an oil. A portion of the product (24.7 g) was dissolved in dichloromethane and filtered through a pad of about 200 g of silica gel. The pad was washed with 1.6 L of dichloromethane:methanol (9:1), and the filtrate was evaporated in vacuo to produce 22.7 g of the title compound.

$^1$H NMR (CDCl$_3$,$\delta$): 1.0 (3H,t), 1.2–2.05 (6H, m), 3.5–3.9(4H,m), 4.73(2H,t), 7.6(2H, broad, amino and hydroxy protons).

EXAMPLE 8

1-Butoxy-2-[3-(3-piperidinomethylphenoxy)-propylamino]-1-cyclobutene-3,4-dione

A.

1-Butoxy-2-(3-benzenesulfonylpropylamino)-1-cyclobutene-3,4-dione

A solution of 1-butoxy-2-(3-hydroxypropylamino)-1-cyclobutene-3,4-dione [prepared in Example 7] (1.14 g, 5.0 mmol) and pyridine (0.65 mL, 8.0 mmol) in 6.0 mL of dichloromethane cooled to 0° C. was treated dropwise with benzenesulfonyl chloride (0.65 mL, 5.1 mmol). The mixture was stirred at ambient temperature for 3 hours, then washed with water (4 times), dried and evaporated under reduced pressure to give 1.53 g (83% yield) of title compound which was used without purification in the subsequent reaction.

$^1$H NMR (CDCl$_3$,$\delta$): 0.93 (3H, t), 1.1–2.3 (6H, m), 3.60 (2H, m), 4.12 (2H, t), 4.67 (2H, t), 7.3–8.1 (7H, m).

B.

1-Butoxy-2-[3-(3-piperidinomethylphenoxy)-propylamino]-1-cyclobutene-3,4-dione

A mixture of 1-butoxy-2-(3-benzenesulfonyl-propylamino)-1-cyclobutene-3,4-dione (1.36 g, 3.70 mmol) [prepared in Step A], 1-piperidinomethyl-3-phenol (0.71 g, 3.7 mmol), dimethylformamide (7 mL) and potassium carbonate (0.69 g, 5.0 mmol) was heated at 50°–70° C. for 5.5 hours then allowed to stand at ambient temperature overnight. The reaction was diluted with water and extracted with ethyl acetate. The organic extracts were washed several times with water and brine, dried, and the solvent was evaporated under reduced pressure to give a brown residue. The desired product which is identical to Example 2 could be isolated by silica gel chromatography using dichloromethane:methanol (95:5) as the eluant in about 21% yield (320 mg).

EXAMPLE 9

1-Butoxy-2-(3-methanesulfonylpropylamino)-1-cyclobutene-3,4-dione

A solution of 1-butoxy-2-(3-hydroxypropylamino)-1-cyclobutene-3,4-dione [prepared in Example 7] (1.0 g, 4.4 mmol) in 5 mL of pyridine was cooled to 0° C. and treated dropwise with 0.36 mL (4.6 mmol) of methanesulfonyl chloride. The mixture was stirred at ambient temperature for 1 hour then poured into 80 mL of water and extracted with 20 mL of ethyl acetate. The organic phase was washed 4 times with water, dried and evaporated to give 0.84 g of title compound.

$^1$H NMR (CDCl$_3$, $\delta$: 0.90 (3H, t), 1.1–2.3 (6H, m), 3.03 (3H, s), 3.6 (2H, broad), 4.3 (2H, t), 4.67 (2H, t), 7.3 (1H, broad).

EXAMPLE 10

1-Butoxy-2-(3-bromopropylamino)-1-cyclobutene-3,4-dione

A. 1,2-Dibutoxy-1-cyclobutene-3,4-dione

A mixture of 1-butanol (3 L), toluene (2 L) and 1,2-dihydroxy-1-cyclobutene-3,4-dione (1 kg; 8.767 moles) was refluxed with stirring under a Dean-Stark separator until water stopped passing over (theory:0.316 L). The excess toluene and butanol were then removed by distillation under reduced pressure to give the title compound as a yellow liquid. The concentrate was diluted with methanol (1.5L) and used in the next step.

B.

1-Butoxy-2-(3-brompropylamino)-1-cyclobutene-3,4-dione

In another flask, 3-bromopropylamine hydrobromide (1.977 kg; 8.849 moles) was added with stirring to a cooled solution of sodium hydroxide (0.35 kg; 8.745 moles) in methanol (5.5L) and stirred for 30 minutes to give a hazy solution of bromopropylamine base.

The solution of bromopropylamine base, cooled to 0° C., was slowly added dropwise with vigorous stirring and cooling to maintain the temperature below to the methanolic solution of Step A containing 1,2-dibutoxy-1-cyclobutene-3,4-dione. The mixture was stirred at 20° C. for 2 hours, polish filtered through diatomaceous earth, washed with methanol (2×0.25L) and the filtrate was added over a period of 1 hour with vigorous stirring to water (31.1L). The mixture was stirred at 0° C.

for 2 hours. The solid was collected by filtration, washed with water (3×2L) and dried to vacuo at 50° C. to give 2137 g (84% yield) of the title compound as an off-white solid; m.p.=69° C.

EXAMPLE 11

1-Butoxy-2-[3-(3-piperidinomethylphenoxy)-propylamino]-1-cyclobutene-3,4-dione

A mixture of 3-piperidinomethyl phenol (0.876 kg; 4.582 moles), 1-butoxy-2-(3-bromopropylamino)-1-cyclobutene-3,4-dione [prepared in Example 10] (1 kg; 3.446 moles), finely powdered (pulverized) potassium carbonate (0.633 kg; 4.582 moles), tris[2-(2-methoxyethoxy)ethyl]amine (0.234 kg; 0.725 mole) in dichloromethane (17.23L) was stirred at 20° C. for 40 hours. The mixture was washed with 3% aqueous sodium hydroxide (2×3L) and then the organic phase was concentrated to dryness under reduced pressure to an oil. The concentrate was diluted with toluene (10L), washed with water (3×2.5L), then extracted with 3N hydrochloric acid (2×2.5L). The cooled aqueous acidic phase was basified with 30% sodium hydroxide then extracted with dichloromethane (2×2.5L). The organic phase was treated with charcoal, stirred for 15 minutes, dried (over magnesium sulfate), filtered through diatomaceous earth and the pad washed with dichloromethane (3×0.25L). The combined filtrate was concentrated to dryness under reduced pressure to give 1300 g (94% yield) of the title compound as a yellowish oil.

EXAMPLE 12

1-Amino-2-[3-(3-piperidinomethylphenoxy)-propylamino]-1-cyclobutene-3,4-dione hydrochloride A mixture of 1-butoxy-2-[3-(3-piperidinomethylphenoxy)propylamino]-1-cyclobutene-3,4-dione [prepared in Example 11] (1 kg; 2.496 moles), 25% ammonium hydroxide (3.33L) in dimethylformamide (8L) was stirred at 20° C. for 20 hours. Excess ammonium hydroxide and water were removed by distillation under reduced pressure. To the concentrate was added 36% hydrochloric acid (0.47L) and the mixture was heated at 75° C. If necessary, water was added to obtain a complete solution. This solution was treated with charcoal (0.05 kg), stirred at 75° C. for 15 minutes, filtered through diatomaceous earth and the pad washed with isopropyl alcohol (3×0.33L). Acetone (6.68L) was added to the filtrate and the mixture was stirred at 5° C. for 3 hours. The solid was collected by filtration, washed with acetone (3×0.5L) and dried in vacuo to give 623 g (66% yield) of the title compound as a light yellow powder.

A sample of the product (1 kg; 2.632 moles) in isopropyl alcohol (4 L) and water (1.7 L) was heated until solution was complete (75° C.). Some insolubles were filtered off and acetone (1.7L) was added to the filtrate. The mixture was stirred at 5° C. for 3 hours. The solid was collected by filtration, washed with acetone (3×0.7L) and dried in vacuo to give 850 g (85% yield) of recrystallized title compound.

EXAMPLE 13

1-(2,2-Dimethylpropoxy)-2-(3-bromopropylamino)-1-cyclobutene-3,4-dione

A solution of neopentyl alcohol (600 g, 6.82 moles) and toluene (1200 mL) was refluxed in suspension with 1,2-dihydroxy-1-cyclobutene-3,4-dione (230 g, 2.02 moles). Water was collected from the stirred mixture with a Dean-Stark separator. After water collection had stopped (ca. 11.5 hours) a clear, orange, homogeneous solution resulted. Reflux was continued and toluene (700 mL) was collected over an additional 1.5 hours. The solution was removed from reflux at this point and cooled to room temperature. Triethylamine (255 g, 2.50 moles) was added in a single portion to the stirred, room temperature solution. To this was added over 0.5 hour, a solution of bromopropylamine hydrobromide in absolute methanol (438 g, 2.0 moles of amine salt in 600 mL methanol). After addition was complete, the solution was stirred for an additional 0.5 hour. The mixture was concentrated at reduced pressure (45° C.) to a total volume of about 1500 mL. Water (2000 mL) was added and the solution was again concentrated at reduced pressure until about 1500 mL of distillate had been removed. The thick solution was filtered to isolate a white solid. The solid was recrystallized from 800 mL of warm isopropanol with gradual cooling to room temperature and −5° C. The product was collected by filtration, washed with two separate 500 mL portions of 1:1 hexane:isopropanol and dried at 45° C., aspirator pressure to a constant weight. The title compound was obtained as a white to very pale yellow powder, m.p. 111°–113° C., yield 528.4 g (86%).

EXAMPLE 14

1-(2,2-Dimethylpropoxy)-2-[3-(3-piperidinomethylphenoxy)-propylamino]-1-cyclobutene-3,4-dione A slurry of 1-(2,2-dimethylpropoxy)-2-(3-bromopropylamino)-1-cyclobutene-3,4-dione prepared in Example 13 (60.8 g, 0.20 mole), 1-piperidinomethyl-3-phenol (76.4 g, 0.4 mole), and tetrabutylammonium bromide (6.44 g, 0.02 mole) was prepared in 400 mL of 1,2-dichloroethane. To this was added a solution of solid potassium carbonate (55.2 g, 0.40 mole) previously dissolved in 115 mL of water. The two phases were mixed well by vigorous stirring and the mixture was heated to reflux. After 4.25 hours, stirring was stopped and the reaction was allowed to cool to room temperature. The layers were separated. The upper, organic phase was washed with 2×200 mL of 5% aqueous sodium hydroxide solution and concentrated at aspirator pressure to ca. ¼ its original volume. The residual oil was diluted with 500 mL of toluene and concentrated to a volume of 350 mL at aspirator pressure. Hexane was added (150 mL) and the solution was briefly warmed to ca. 50° C. After cooling to room temperature with stirring, the solution was slowly cooled to −10° C. with stirring and seeding to give a very thick paste. The heavy solution was filtered and washed with 200 mL of ice-cold 2:1 hexane:isopropanol. After drying at aspirator pressure and ambient temperature to a constant weight, 50.9 g, (61.4%) of the title compound was obtained as a light-yellow powder, m.p. 79°–81° C.

EXAMPLE 15

1-Amino-2-[3-(3-piperidinomethylphenoxy)-propylamino]-1-cyclobutene-3,4-dione hydrochloride The neopentyl ester from Example 1 (10.2 g, 0.0246 mole) was dissolved in 95 mL isopropanol by stirring and heating to ca. 50° C. and filtering through filter cel to clarify the solution. This mixture was cooled to −10° C. with stirring and to this was added a −10° C. solution of isopropanol/ammonium hydroxide (12 mL of concentrated ammonia solution titrated to contain 13 moles per liter of ammonia; equals 0.156 mole ammonia in 48 mL isopropanol) over 5 minutes. The temperature was maintained at −10° C. for 0.75 hour and then allowed to warm to ambient temperature over 3.25 hours by removal of the cooling bath. After an additional 4 hours at room temperature, no starting material was seen by HPLC. A thick, off-white product suspension resulted. Excess ammonia was removed at aspirator pressure over 1.5 hours. The suspension was treated with 55 mL of 6:1 isopropanol:concentrated HCl and stirred at room temperature, followed by gradual heating to 45° C. over 0.5 hour. The resulting solution was allowed to cool to room temperature with stirring over 3 hours. The product was collected by filtration and washed with 50 mL of isopropanol. The white powder obtained was dried at room temperature under reduced pressure for 24 hours to give 8.33 g (89% yield) of the title compound as its hydrochloride salt.

EXAMPLE 16

1-(Cyclohexyloxy)-2-(3-bromopropylamino)-1-cyclobutene-3,4-dione

A suspension of squaric acid (23.3 g, 0.20 mole) in cyclohexanol (80 mL, 77 g, 0.77 mole) and toluene (120 mL) was refluxed with continuous collection of water in a Dean-Stark separator. After three hours reflux, the solution was homogeneous and the theoretical amount of water had been collected. The solution was washed with water (100 mL). To the stirred toluene solution of squarate ester was added methanol (100 mL) and triethylamine (58 mL) and then bromopropylamine hydrobromide (42.2 g, 0.193 mole) in 100 mL of methanol over 0.5 hour. After the addition was complete, the reaction was stirred an additional 0.5 hour and then concentrated under reduced pressure at 45° C. (aspirator pressure) to ca. ¼ volume. The resulting thick slurry was diluted with 500 mL water and filtered to isolate a crude, off-white solid. This was recrystallized from 1:1 toluene:hexane (300 mL) to give 45.3 g (74.5% yield) of the title compound as a pale yellow powder, m.p. 68°–70° C.

EXAMPLE 17

1-(2-Methylpropoxy)-2-(3-bromopropylamino)-1-cyclobutene-3,4-dione

Squaric acid (45.6 g, 0.40 mole) was refluxed in suspension with toluene (180 mL) and sec-butyl alcohol (150 mL, 1.64 mole) with collection of the water generated in a Dean-Stark separator. After 12 hours at reflux, water separation had ceased and the theoretical amount of water had been collected. The solution was concentrated at aspirator pressure (45° C.) to a heavy oil. Isopropyl alcohol (800 mL) was now added, followed by triethylamine (45.6 g, 0.45 mole). To the stirred solution was added over ca. 0.5 hour, bromopropylamine hydrobromide as a solid powder (87.6 g, 0.40 mole). After an additional 18 hours stirring at room temperature, the solution was concentrated to give a heavy, white solid. This material was washed thoroughly with water (2×500 mL), filtered and recrystallized from 1:1 hexane:isopropanol (800 mL) at 0° C. After filtration and drying to a constant weight, 92 g of an off-white solid (79.3% yield) was obtained, m.p. 70°–71° C.

What is claimed is:

1. A compound of the formula

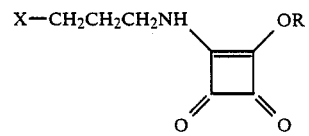

wherein R is lower alkyl or cyclohexyl, X is hydroxy, halogen or —SO$_3$R$^4$ and R$^4$ is lower alkyl, trifluoromethyl, phenyl or substituted phenyl in which said substituent may be methyl, chloro, bromo, methoxy or nitro.

2. A compound of claim 1 wherein X is hydroxy.
3. A compound of claim 1 wherein X is benzenesulfonate.
4. A compound of claim 1 wherein X is halogen.
5. A compound of claim 1 wherein X is bromo.
6. A compound of claim 1 wherein R is butyl.
7. A compound of claim 4 wherein R is sec-butyl.
8. A compound of claim 4 wherein R is neopentyl.
9. A compound of claim 1 which is 1-butoxy-2-(3-bromopropylamino)-1-cyclobutene-3,4-dione.
10. A compound of claim 1 which is 1-(2,2-dimethylpropoxy)-2-(3-bromopropylamino)-b 1-cyclobutene-3,4-dione.

* * * * *

UNITED STATES PATENT AND TRADEMARK OFFICE
CERTIFICATE OF CORRECTION

PATENT NO. : 4,927,970

DATED : May 22, 1990

INVENTOR(S) : James L. Douglas, et al.

It is certified that error appears in the above-identified patent and that said Letters Patent is hereby corrected as shown below:

In Claim 6, Line 43, "claim 1" should read -- claim 4 --.

In Claim 10, Line 49 thereof should read -- propoxy)-2-(3-bromopropylamino)-1-cyclobutene- --

Signed and Sealed this

Third Day of September, 1991

Attest:

HARRY F. MANBECK, JR.

*Attesting Officer*    *Commissioner of Patents and Trademarks*